US008496616B2

(12) United States Patent
Chen

(10) Patent No.: US 8,496,616 B2
(45) Date of Patent: *Jul. 30, 2013

(54) MEDICAL DEVICE EMPLOYING LIQUID CRYSTAL BLOCK COPOLYMERS AND METHOD OF MAKING THE SAME

(75) Inventor: John J. Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/467,642

(22) Filed: May 9, 2012

(65) Prior Publication Data

US 2012/0220932 A1  Aug. 30, 2012

Related U.S. Application Data

(63) Continuation of application No. 12/974,467, filed on Dec. 21, 2010, now Pat. No. 8,187,492, which is a continuation of application No. 12/706,463, filed on Feb. 16, 2010, now Pat. No. 7,857,785, which is a continuation of application No. 11/353,606, filed on Feb. 14, 2006, now Pat. No. 7,662,129.

(51) Int. Cl.
*A61M 29/00* (2006.01)
*A61M 25/10* (2006.01)
*C09K 19/38* (2006.01)
*C08L 77/10* (2006.01)
*C08L 77/12* (2006.01)

(52) U.S. Cl.
USPC .............. 604/96.01; 604/103.01; 604/103.11; 604/264; 604/523; 604/524; 252/299.01; 525/434

(58) Field of Classification Search
CPC .............................. A61L 29/049; A61L 29/126
USPC .................... 604/96.01, 264, 103.01, 103.11, 604/523, 524; 252/299.01; 525/434
See application file for complete search history.

(56) References Cited

U.S. PATENT DOCUMENTS

| | | |
|---|---|---|
| 4,238,599 A | 12/1980 | Langley et al. |
| 4,490,421 A | 12/1984 | Levy |
| 4,663,422 A | 5/1987 | Inoue et al. |
| 4,801,677 A | 1/1989 | Eckhardt et al. |
| 4,912,193 A | 3/1990 | Dicke et al. |
| 4,952,334 A | 8/1990 | Hakemi et al. |
| 5,017,304 A | 5/1991 | Hijikata |
| 5,030,703 A | 7/1991 | Pielartzik et al. |
| 5,156,785 A | 10/1992 | Zdrahala |
| 5,173,562 A | 12/1992 | Wilson et al. |
| 5,248,305 A | 9/1993 | Zdrahala |
| 5,346,970 A | 9/1994 | Dashevsky et al. |
| 5,508,338 A | 4/1996 | Kim et al. |
| 5,565,530 A | 10/1996 | Hattori et al. |
| 5,677,394 A | 10/1997 | Bohme et al. |
| 5,750,626 A | 5/1998 | Shimizu et al. |
| 5,767,198 A | 6/1998 | Shimizu et al. |
| 5,869,574 A | 2/1999 | Shimizu et al. |
| 6,024,722 A | 2/2000 | Rau et al. |
| 6,027,516 A | 2/2000 | Kolobow et al. |
| 6,054,537 A | 4/2000 | Shimizu et al. |
| 6,132,819 A * | 10/2000 | Ober et al. ..................... 428/1.1 |
| 6,242,063 B1 | 6/2001 | Ferrera et al. |
| 6,284,333 B1 | 9/2001 | Wang et al. |
| 6,325,780 B1 | 12/2001 | Schaible et al. |
| 6,328,925 B1 | 12/2001 | Wang et al. |
| 6,443,925 B1 | 9/2002 | Schaible et al. |
| 6,552,127 B1 | 4/2003 | Shimizu et al. |
| 6,596,219 B2 | 7/2003 | Schaible et al. |
| 6,730,377 B2 | 5/2004 | Wang |
| 6,905,743 B1 | 6/2005 | Chen et al. |
| 6,930,166 B2 | 8/2005 | Yamamoto |
| 6,977,103 B2 | 12/2005 | Chen et al. |
| 6,986,785 B2 | 1/2006 | O'Shaughnessy et al. |
| 7,582,078 B2 | 9/2009 | Chen et al. |
| 7,662,129 B2 | 2/2010 | Chen |
| 7,857,785 B2 | 12/2010 | Chen |
| 7,914,485 B2 | 3/2011 | Chen et al. |
| 8,187,492 B2 | 5/2012 | Chen |
| 2003/0091765 A1 | 5/2003 | Ferrera et al. |
| 2005/0142314 A1 | 6/2005 | Burgmeier et al. |

FOREIGN PATENT DOCUMENTS

| | | |
|---|---|---|
| JP | 107779 | 1/1998 |
| JP | 10095821 | 4/1998 |
| JP | 2001-527119 | 12/2001 |
| WO | 9748782 | 12/1997 |
| WO | 02056930 | 7/2002 |

OTHER PUBLICATIONS

Arai et al., "Role of network nematicity in swelling and phase equilibria of polymer networks in nematic solvents", Polymer, 45, (2004), pp. 5127-5135.
Chen, Bor-Kuan, et al., "Synthesis and Properties of Liquid Crystalline Polymers with Low Tm and Broad Mesophase Temperature Ranges," Polymer, 46 (2005), 8624-8633.
Gopalan, Padma, et al., "Rod-Coil Block Copolymers: An Iterative Synthetic Approach via Living Free-Radical Procedures," Journal of Polymer Science: Part A: Polymer Chemistry, vol. 41 (2003) 3640-3656.
Hakemi, H., "On the Miscibility of Liquid Crystalline Polymers," Polymer, 41 (2000) 6145-6150.
Hurdoc, Nicolae, et al., "Thermal Behaviour and Molecular Modeling of Some Aromatic Polyethers Containing a Hexamethylenic Spacer," Polymer Degradation and Stability, 72 (2001), 441-445.
Liu, Yingliang, et al., "Synthesis and Characterization of Liquid Crystalline Copolyesters Containing Horizontal and Lateral Rods in Main Chain (II)," Reactive & Functional Polymers, 64 (2005) 35-46.

(Continued)

*Primary Examiner* — Shean C Wu
(74) *Attorney, Agent, or Firm* — Vidas, Arrett & Steinkraus, P.A.

(57) ABSTRACT

A medical device, at least a portion of which is formed from a polymer composition including at least one liquid crystal block copolymer having at least one A block and at least one B block wherein the A block is formed of mesogenic repeat units and the B block is a soft block.

20 Claims, No Drawings

OTHER PUBLICATIONS

Makaruk, Leszek, et al., "Mesophase Transitions in Liquid Crystal Polymers," Reactive & Functional Polymers, 33 (1997) 225-231.

Ober et al. "Liquid Crystal Polymers. V. Thermotropic Polyesters with Either Dyad or Triad Aromatic Ester Mesogenic Units and Flexible Polymethylene Spacers in the Main Chain," Polymer Journal, vol. 14, No. 1, pp. 9-17 (1982).

http://www.sharpsma.com/lcd/lcdguide/Primer/crystal-intro.php, "Liquid Crystal Physics" pp. 1-3.

http://www.cem.msu.edu/~reusch/VirtualText/polymers.htm, "Polymers" pp. 1-19.

http://plc.cwru.edu/tutorial/enhanced/files/plc/mc_plc/MC_plc.htm, "Main Chain Polymer Liquid Crystals" pp. 1-2.

http://en.wikipedia.org/wiki/Mesogen, "Mesogen" pp. 1.

\* cited by examiner

MEDICAL DEVICE EMPLOYING LIQUID CRYSTAL BLOCK COPOLYMERS AND METHOD OF MAKING THE SAME

CROSS-REFERENCE TO RELATED APPLICATIONS

This application is a continuation of U.S. patent application Ser. No. 12/974,467 filed Dec. 21, 2010, which is a continuation of U.S. patent application Ser. No. 12/706,463 filed Feb. 16, 2010, issued as U.S. Pat. No. 7,857,785 on Dec. 28, 2010, which is a continuation of U.S. patent application Ser. No. 11/353,606 filed Feb. 14, 2006, issued as U.S. Pat. No. 7,662,129 on Feb. 16, 2010 which are hereby incorporated by reference.

FIELD OF THE INVENTION

The present invention relates to the field of insertable and/or implantable medical devices, particularly to balloon catheter assemblies and components thereof.

BACKGROUND OF THE INVENTION

It is known to use liquid crystal polymers (LCPs) in combination with thermoplastic polymers, i.e. matrix polymers, for use in the manufacture of insertable and/or implantable medical devices such as catheter assemblies and components thereof such as inflatable medical balloons which can be disposed at the distal end of a balloon catheter assembly. For example, see commonly assigned U.S. Pat. Nos. 6,977,103, 6,905,743, 6,730,377 and 6,284,333. See also U.S. Pat. Nos. 6,596,219, 6,443,925 and 6,325,780 to Schaible.

Liquid crystal polymers are known to phase separate from commonly used thermoplastic polymers into multiphase polymer compositions. For example, see U.S. Pat. Nos. 5,248,305 and 5,156,785 to Zdrahala.

Compatibilized blends of LCP and thermoplastic polymers have been found suitable for use as medical device balloon materials. See for example commonly assigned U.S. Pat. No. 6,242,063.

It would be desirable to have a liquid crystal polymer material or blend using a liquid crystal polymer material which has increased compatibility over other previous LCP/polymer blends which could be employed in the formation of medical devices, particularly in the manufacture of catheter assemblies or components thereof.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The present invention relates to polymer compositions useful in the formation of medical devices which include at least one liquid crystal block copolymer having at least one A block and at least one B block.

The A block, which may also be referred to herein as the mesogenic (liquid crystal) block, may include any suitable mesogenic repeat (monomer) unit. As used herein, the term "mesogenic" shall be used to refer to those repeat units which impart liquid crystal properties, such as stiffness and restriction to rotation, to the polymer. The term "mesogenic unit" as employed herein, shall be used to refer to any monomer having a mesogen, as well as those monomers including spacers such as methylene groups, therein.

Any suitable mesogenic repeat unit may be employed herein. Suitably, the A block has at least one aromatic group per each mesogenic repeat unit and more suitably the A block has at least two aromatic groups per each mesogenic repeat unit.

The B block is the soft block. Suitably, the B block is aliphatic. Suitably the B block has less than 10% aromaticity by weight of the B block, more suitably less than 5% aromaticity by weight of the B block and most suitably substantially no aromaticity.

The polymers may be formed using conventional reaction techniques such as condensation reactions as will be described in more detail below.

These polymers may be employed alone, or in combination with other polymers.

The polymers find particular utility in the formation of medical devices such as catheter assemblies and components thereof, including, for example, shafts, tips, manifolds and balloons.

These and other aspects, embodiments and advantages of the present invention will become immediately apparent to those of ordinary skill in the art upon review of the Detailed Description and Claims to follow.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The present invention relates to polymer compositions useful in the formation of medical devices or at least a portion of a medical device. The polymer compositions include at least one liquid crystal block copolymer having at least one A block and at least one B block.

The A block is formed from mesogenic (liquid crystal) repeat units. As employed herein, the term "mesogenic" shall be used to refer to those repeat units (monomers) which impart liquid crystal properties to the polymer. The mesogenic repeat unit may include a mesogen, as well as any spacers such as methylene groups. Liquid crystal polymers have a third phase of matter which exists between a crystalline (solid) and an isotropic (liquid) phase, that has properties between those of a conventional liquid, and those of a solid crystal. For instance, a liquid crystal (LC) may flow like a liquid, but have the molecules in the liquid arranged and oriented in a crystal-like way. It is the mesogen of the mesogenic repeat unit which induces the structural order, rigidity and necessary restriction on movement that allows the polymer to display these liquid crystal properties. The mesogen is typically made up of one or more aromatic rings. Suitably, each mesogenic repeat unit has at least one aromatic group per each repeat unit, and more suitably each mesogenic repeat unit has at least two aromatic groups per each repeat unit.

The B block is the soft block of the liquid crystal block copolymer. Suitably, the B block is aliphatic. Suitably, the B block has less than 10% aromaticity by weight of the B block, more suitably the B block has less than 5% aromaticity by weight of the B block, and most suitably the B block has substantially no aromaticity.

The block copolymers may be of the general formula A-B diblock, $(A-B)_n$ wherein n is 3 to 20, B-$(A-B)_n$-B wherein n is 3 to 20, A-B-A triblock, B-A-B triblock having soft segments at the free chain end, A-B-A-B-A pentablock, multiblock polymers such as A-B-C or A-C-B triblock, B-$(A-B-C)_n$-B wherein n is 3 to 20, random block copolymers, etc.

The above list is intended for illustrative purposes only, and not as a limitation on the scope of the present invention.

The A block, which may also be referred to herein as the mesogenic block, may include any suitable mesogenic repeat unit. Suitably, the mesogenic repeat unit has at least one aromatic group per unit, and more suitably the mesogenic repeat unit has at least two aromatic groups per unit. The A block of the liquid crystal block copolymer is characterized by mesogenic repeat units which can provide the liquid crystal block copolymer with stiffness resulting from restriction on rotation caused by steric hindrance and resonance. For example, aromatic ring(s) can provide both steric hindrance and resonance. Some mesogenic repeat units may include both aromatic and aliphatic rings.

The A block may contain any number of repeating units up to about 50.

Suitably, the mesogenic block has an axial ratio, defined by the length of the molecule divided by the diameter (x=L/d), of at least three. This axial ratio provides the mesogenic block with rod-like characteristics.

A variety of suitable mesogenic repeat units find utility in the formation of the A block of the liquid crystal block copolymer.

Classes of aromatic structural groups useful in the formation of each mesogenic repeat unit include, but are not limited to, aromatic dicarboxylic acids, aromatic hydroxycarboxylic acids, aromatic aminocarboxylic acids, diphenols, and aminophenols, for example.

Examples of useful aromatic dicarboxylic acids include, but are not limited to, 1,4-naphthalenedicarboxylic acid, 1,5-naphthalenedicarboxylic acid, 2,6-naphthalenedicarboxylic acid, biphenyl-4,4'-dicarboxylic acid, biphenyl-3,3'-dicarboxylic acid, diphenoxyethane-4,4'-dicarboxylic acid, diphenyl ether-4,4'-dicarboxylic acid, methylterephthalic acid, methoxyterephthalic acid, chloroterephthalic acid, 4-chloronaphthalene-2,7-dicarboxylic acid, 1,3-naphthalenedicarboxylic acid, 1,6-naphthalenedicarboxylic acid, 1,7-naphthalenedicarboxylic acid, 2,7-naphthalenedicarboxylic acid, biphenyl-3,4'-dicarboxylic acid, diphenyl ether-3,4'-dicarboxylic acid, 4-methylisophthalic acid, 5-methylisophthalic acid, diphenyl ether-4,4'-dichloro-3,3'-dicarboxylic acid and iso- and terephthalic acid.

Examples of useful aromatic hydroxycarboxylic acids include, but are not limited to, 4-hydroxy-3-methylbenzoic acid, 4-hydroxy-3-phenyl-benzoic acid, 4-hydroxy-2-ethyl-benzoic acid, 3-chloro-4-hydroxy-benzoic acid, 4-hydroxy-3-methoxybenzoic acid, hydroxyl benzoic acid including 4-hydroxybenzoic acid and 3-hydroxybenzoic acid, hydroxynaphthoic acid including 6-hydroxy-2-naphthoic acid, etc.

Examples of useful diphenols include, but are not limited to, hydroquinone, t-butylhydroquinone, bromohydroquinone, chlorohydroquinone, methylhydroquinone, ethylhydroquinone, phenylhydroquinone, 4,4'-dihydroxydiphenyl, 4,4'-dihydroxydiphenyl ether, 4,4'-dihydroxydiphenylethane, 4,4'-dihydroxydiphenoxyethane, 3,5'-dihydroxydiphenyl, 4-hydroxy-4'-carboxydiphenyl, 3,5'-dihydroxydiphenyl ether, naphthalene, dihydroxynaphthalene including 1,4-, 1,5- and 2,6-dihydroxynaphthalene, for example, 4-methoxy-2,6-dihydroxynaphthalene, 1,3-dihydroxynaphthalene, 1,6-dihydroxynaphthalene, 1,7-dihydroxynaphthalene, 2,7-dihydroxynaphthalene, 2,5-dichloro-1,6-dihydroxynaphthalene, 4-methoxy-2,7-dihydroxynaphthalene, 2,2'-dimethyl-4,4'-dihydroxydiphenyl, 3,3',5,5'-tetramethyl-4,4'-dihydroxydiphenyl, 3,5'-dimethoxy-4,4'-dihydroxydiphenyl ether, 1,2-(2-chloro-4-hydroxyphenoxy)-ethane resorcinol, 3,4'-dihydroxydiphenyl, 3,4'-dihydroxydiphenyl ether, 3,4'-dihydroxydiphenoxyethane, 4-chlororesorcinol, 4-bromoresorcinol, 4-methylresorcinol, 4-phenylresorcinol, 4-ethoxyresorcinol, etc.

Examples of aromatic aminocarboxylic acids include, but are not limited to, 2-aminobenzoic acid, 3-aminobenzoic acid, 4-aminobenzoic acid, 4-chloroanthranilic acid, 5-chloroanthranilic acid, 3-amino-4-chlorobenzoic acid, 4-amino-3-phenyl-benzoic acid, 4-amino-3-methoxybenzoic acid, 4-amino-3-phenoxybenzoic acid, 6-amino-5-chloro-2-naphthoic acid, 6-amino-5-methyl-2-naphthoic acid and 6-amino-5-methoxy-2-naphthoic acid, etc.

Examples of aminophenols include, but are not limited to, 3-aminophenol, 5-amino-2-chlorophenol, 4-aminophenol, 3-amino-2-methylphenol, 3-amino-4-methylphenol, 5-amino-1-naphthol, 6-amino-1-naphthol, 8-amino-2-naphthol, 6-amino-2-naphthol and 4-amino-1-hydroxy-biphenyl, etc.

Other groups which may be included in the mesogenic repeat unit include paraphenylene (—Ar—) wherein Ar represents an aromatic ring, as well as substituted paraphenylenes such as para-diacetoxyphenylene (—CH$_2$COOCH2—Ar—CH$_2$COOCH$_2$—).

Any combination of such groups may also be incorporated into the repeat unit in the LC block of the LC block copolymer. For a discussion of these structural groups, see for example, U.S. Pat. Nos. 4,663,422 and 5,017,304 and 5,030,703 for a discussion of such structural units, each of which is incorporated by reference herein in its entirety. See also U.S. Pat. Nos. 4,238,599, 4,801,677, 5,173,562, each of which is incorporated by reference herein in its entirety, for further examples of suitable mesogenic units.

Other suitable mesogenic repeat units include those of the following general formula:

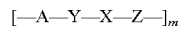

wherein X can be $(CH_2)_n$ wherein n is an integer from about 2 to about 10, m can range from about 2 to about 50, Y and Z can each independently be —COO or —CONH or can be a single bond between two carbon atoms, and A can be p-phenylene, 1,4-naphthylene, 2,6-naphthylene or 1,5-naphthylene, monosubstituted phenylene with methyl, chloro or phenyl substitution, —ArCH=CHAr— wherein AR is a phenyl ring, —Ar—COOAr—, —Ar—CONHAr—, or —Ar—OOC—Ar—COO—AR—, etc. For a discussion of such mesogenic repeat units, see U.S. Pat. No. 4,952,334, the entire content of which is incorporated by reference herein.

Another specific example of a suitable aromatic mesogenic repeat unit has the structure —Ar—CO—NH—Ar—NH—CO—Ar—.

Other suitable mesogenic repeat units which can be employed herein are described by Ober et al. in Polymer Journal, Vol. 14, No. 1, pp. 9-17 (1972) and have the following structure:

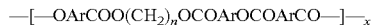

wherein Ar represents phenyl with para-bond sites, n may range from about 2 to about 10, and x can range from about 2 to about 50. These mesogenic units can be characterized as aromatic ester mesogenic units comprising three linearly-aligned aromatic rings.

The type of mesogenic repeat unit represented by the formula above, wherein Ar represents phenyl with para-bond sites, n is an integer of from about 2 to about 10, and x is an integer of from about 5 to about 15, is described in U.S. Pat. No. 5,508,338, the entire content of which is incorporated by reference herein.

Other specific examples of suitable mesogenic repeat units include poly(hydroxynaphthoic acid) (—O—ArAr—CO—, wherein ArAr is two fused benzene rings) and poly(p-phenyleneterephthlate) (—O—Ar—OOC—Ar—CO—).

Another specific example of a suitable LC block employs a combination of hydroxybenzoic and hydroxynaphthoic acid and has repeating units of the formula —[—O—AR—CO—]$_x$—[—O—ArAr—CO—]$_y$— wherein x and y are positive numbers of 1 or more, for instance, x and y may vary independently from about 1 to about 50, and suitably about 1 to about 25. In some embodiments x=y=1 and in other embodiments x≠y. See, for example, U.S. Pat. Nos. 6,552,127, 6,054,537, 5,869,574, 5,767,198 and 5,750,626, each of which is incorporated by reference herein in its entirety.

Another example of a mesogenic unit formed using a combination includes that shown in U.S. Pat. No. 4,912,193, the entire content of which is incorporated by reference herein, employing a combination of p-hydroxy benzoic acid, 4,4'-dihydroxy diphenyl, terephthalic acid, and isophthalic acid.

The mesogenic repeat unit of the present application may be said to include both a mesogenic portion and a spacer. The mesogenic repeat units of the A block can be attached together in such a way that the mesogen portion of the mesogenic repeat unit forms a part of the backbone (main chain liquid crystal polymer structure), or they may be attached together in such a way that the mesogen is attached to the polymer backbone as a pendant group (side chain liquid polymer structure). Examples of mesogenic repeat units employed in main chain liquid crystal polymers wherein the mesogen portion of the mesogenic repeat unit forms a part of the backbone is hydroxynaphthoic acid, and poly(p-phenyleneterephthalate).

An example of a mesogenic repeat unit resulting in a side chain liquid crystal polymer structure has the following structure:

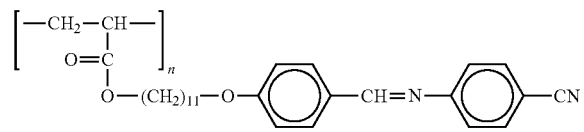

The A block or LC block of the liquid crystal block copolymer may be made using any method known in the art. Most are made using conventional condensation reactions. See for example Chen, Bor-Kuan, et al., "Synthesis and properties of liquid crystalline polymers with low Tm and broad mesophase temperature ranges," *Polymer,* 46 (2005) 8624-8633, Hurdoc, Nicolae, et al., "Thermal behaviour and molecular modeling of some aromatic polyethers containing a hexamethylenic spacer," *Polymer Degradation and Stability,* 72 (2001) 441-445, Liu, Yingliang, et al., "Synthesis and characterization of liquid crystalline copolyesters containing horizontal and lateral rods in main chain (II)," *Reactive & Functional Polymers,* 64 (2005) 35-46, Makaruk, Leszek, et al., "Mesophase transitions in liquid crystal polymers", *Reactive & Functional Polymers,* 33 (1997) 225-231, Gopalan, Padma, et al., "Rod-Coil Block Copolymers: An Iterative Synthetic Approach via Living Free-Radical Procedures," *Journal of Polymer Science: Part A: Polymer Chemistry,* Vol. 41, (2003) 3640-3656, Hakemi, H., "On the miscibility of liquid crystalline polymers," *Polymer,* 41 (2000) 6145-6150, each of which is incorporated by reference herein in its entirety.

Whereas it is the A block of the liquid crystal block copolymer which provides the block copolymer with strength, stiffness and rigidity, the B block of the liquid crystal block copolymer is the soft segment of the block copolymer and provides the polymer with flexibility. Suitably, the B block is aliphatic. Suitably, the B block has less than 10% aromaticity by weight of the B block, more suitably less than 5% by weight of the B block, and most suitably, the B block has substantially no aromaticity. Suitably, the B block is derived from repeating units of olefins, esters, ethers, amides, and siloxanes, for example.

Examples of suitable repeating units for formation of the B block include, but are not limited to, amides, esters, ethers, imides, olefins and siloxanes.

In some embodiments, the B block is formed from hydrophilic monomer units. Examples of suitably hydrophilic monomers include, but are not limited to, short chain aliphatic ethers such as polyethylene oxide glycol or polytetramethylene oxide glycol which are the chain ends of hydrophilic macromolecules, diols or dicarboxylic acids containing a metal sulfonate group, oligomers such as polyalkylene glycol copolymerized with other monomers such as aliphatic dicarboxylic acids, hydrophilic acrylates available from Sartomer such as polyethylene glycol diacrylate, acrylamides and N,N-dimethylacrylamide, N-vinylpyrrolidone, etc.

The above lists are intended for illustrative purposes only, and not as a limitation on the scope of the present invention.

The A block may have anywhere from about 2 to about 50 repeating units, and more suitably about 2 to about 25 repeating units, and the B block may have anywhere from about 2 to about 25 repeating units, and suitably about 2 to about 10 repeating units.

In embodiments wherein the block copolymer further has a C block, the mesogenic units of the C block may be selected from those mesogenic repeat units discussed as useful in forming the A block. However, in a liquid crystal polymer having both an A block and a C block, the C block is formed from different mesogenic repeat units than those of the A block. For example, in one embodiment, the A block of the liquid crystal block copolymer is a polyamide segment formed using and the C block is a polyester segment formed using aromatic hydroxycarboxylic acids, for example. Examples of suitable mesogenic units for formation of the polyamide A block structure include, for example,

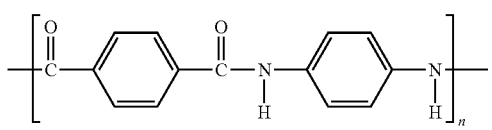

This portion of the liquid crystal block copolymer can be made by the condensation reaction between HOOC—AR—COOH (benzene-1,4-dicarboxylic acid) and $H_2N$—AR—$NH_2$(1,4-diaminobenzene) to form the following structure:

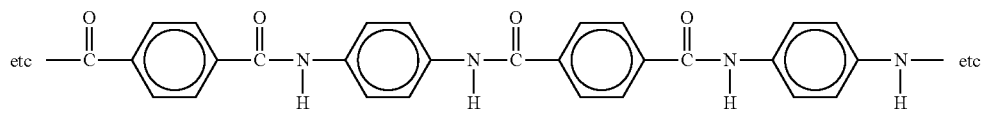

In this embodiment, suitable B blocks may be formed by condensation of hexanedioic acid and hexamethylenediamine (nylon 6,6), ring opening polymerization of caprolactam (nylon 6) or ring opening polymerization of laurolactam (nylon 12), for example.

Nylon 6 (polycaprolactam) is not a condensation polymer, but rather is formed by the ring opening polymerization of caprolactam monomers.

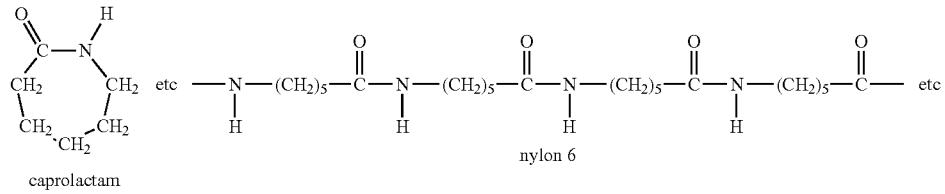

Nylon 6,6, on the other hand, is formed by condensation between hexandioic acid (adipic acid) and 1,6-diaminohexane (hexamethylenediamine): repeating unit:

$H_2N(CH_2)_6NH_2$+$HOOC(CH_2)_4COOH$→[—NH—$(CH2)_6$—NH—$CO(CH2)_4$—CO—]$_n$+$H_2O$

Hexanedioyl dichloride may be used in place of hexanedioic acid.

The liquid crystal polyester A block, the nylon B block and the liquid crystal polyamide C block can be connected via conventional condensation reactions.

The C block may also have anywhere from about 2 to about 50 repeating units, and more suitably anywhere from about 2 to about 25 repeating units.

The above lists are intended for illustrative purposes only, and not as a limitation on the scope of the present invention.

Suitably, the A block is from about 50% to about 95% by weight of the block copolymer and the B block is about 5% to about 50% by weight of the block copolymer, more suitably, the B block is about 10% to about 30% by weight of the block copolymer. In some embodiments, the B block or soft segment is about 10% or less by weight of the LC block copolymer.

Any suitable method of polymerization may be employed depending on the monomers, oligomers, or polymers which are employed. Most commonly, the polymerization can be accomplished via condensation reactions which are achieved through reacting molecules incorporating alcohol, amine or carboxylic acid (or other derivative) functional groups. An ether, amide, or ester linkage is formed and a small molecule, commonly water, is released. Thus, only a part of the monomer becomes part of the polymer.

Addition polymerization, wherein the entire monomer becomes part of the polymer, may also be employed. For example, anionic polymerization can be used to prepare block copolymers. In such a process, a reactive site remains at the end of the chain until it is quenched. The unquenched polymer may be referred to as a living polymer, and the addition of a second monomer can result in a block polymer. These processes may be employed where reactive unsaturated sites, i.e. double or triple bonds, are present. Most addition polymerizations are also chain growth polymerizations wherein one monomer is added at a time, although there are exceptions.

EXAMPLE

In a specific example 4-hydroxy-2-benzoic acid (HBA) may be acetylized to 4-acetoxybenzoic acid (ABA) with acetic anhydride as the solvent in the presence of a catalytic amount of sodium acetate in the manner of Chen et al, "Synthesis and properties of liquid crystalline polymers with low $T_m$ and broad mesophase temperature ranges," *Polymer*, 46 (2005) 8624-8633. Still following the method of Chen et al, ABA then may be reacted with 1,4-butanediol (BDO) in a molar ratio of about 1:3 and $Sb_2O_3$ catalyst in an amount of about 300 ppm to produce the ester ABA-BDO-ABA.

Polymerization is then accomplished by adding a mixture of the ester ABA-TMG-ABA, terephthalic acid (TPA), a nylon 6 polymer terminated on both ends with acid groups (Ny6) and 250-300 ppm of $Sb_2O_3$ or $Ti(OBu)_4$ catalysts to a flask with a nitrogen purge using a molar ratio of the ester to TPA to Ny6 dicarboxylic acid of 1.0:0.67:0.33. The nitrogen outlet is equipped with a distillation column with vacuum. The mixture is heated at melt for about 5 hours at a temperature of about 200° C. to about 250° C., depending on the temperature necessary to melt the mixture. Thermal stabilizers and antioxidants such as Irganox® 1010 available from Ciba-Geigy are used added to inhibit decomposition. The mixture is stirred, for instance at 200 rpm once the melt temperature has been reached. The nitrogen flow is regulated to prevent evaporation of reactants. After about 3-5 hours the temperature is gradually increased to about 280° C. and the acetic acid produced by condensation is removed by distillation. When no more distillate is observed a vacuum of about 10 torr is applied for 2-3 hours and then the vaccuum is reduced to 1-2 torr and the mixture stirred continuously for an additional 4 hrs, all the while maintaining the temperature at about 280° C. The product is then allowed to cool. Monomers and oligomers may be removed by Soxhlet extraction using acetone.

The resultant polymer is an A-B-A block copolymer having a structure of [(ABA-BDO-ABA-TPA)$_x$ ABA-BDO-ABA]-Ny6-[ABA-BDO-ABA-(TPA-ABA-BDO-ABA)$_y$].

In modifications of the above equivalent amounts of ethylene glycol or 1,3 propane diol may be substituted for 1,4-butanediol, 6-hydroxy-2-naphthoic acid may be substituted for 4-hydroxy benzoic acid, 2,6-naphthalene dicarboxylic acid may be substituted for TPA, and/or other diacid terminated nylon polymers such as nylon 6,10 or nylon 9,12, may be substituted for the nylon 6 polymer. An A-B diblock copolymer may be synthesized in a similar manner using a mono-acid terminated nylon polymer such as nylon 12, in place of the nylon 6 diacid. Furthermore the relative ratio of short diacid to acid terminated nylon can be varied over a very wide range for instance from about 1:10 to about 1:10 on an acid equivalents basis.

The liquid crystal block copolymer of the invention may itself be employed in the formation of medical devices or components thereof, or, the liquid crystal block copolymer may be blended with another polymer or polymers. In the latter case, suitably, the polymer and the B block may be selected so as to be compatible with one another. Compatibility, as used herein, refers to compatibility on both the macroscopic and microscopic, i.e. molecular, scale. Thus, compatibility on a macroscopic scale, may refer to those polymer blends which do not exhibit gross phase separation.

In polymer mixtures, the matrix polymer may interact strongly with the LC block copolymer or one block of the LC block copolymer, thus providing desirable polymer properties.

In mixtures wherein the LC block copolymer is blended with other polymers, at least one other polymer of the blend, may be selected from those polymers which are non-liquid crystal polymers. Examples of suitable polymers which may be used for blending with the LC block copolymer described herein include, but are not limited to, polyesters and copolyesters, polyamides, polyethers, polyimides, polyolefins and silicones, for example. These polymers are intended for illustrative purposes only, and not as a limitation on the scope of the present invention.

Specific examples of suitable polymers which may be employed in a blend include polyamide elastomers such as those sold under the tradename of PEBAX® available from Arkema, headquarters in Paris, France, and polyester elastomers such as those sold under the name of HYTREL® available from DuPont in Dover, Del. are also suitable for use.

For example, if the liquid crystal block copolymer is blended with a poly(ether-block-amide) copolymer having an (AB)$_n$ block copolymer structure wherein the A block is nylon and the B block is polytetramethylene oxide, a suitable LC block copolymer B block may include amide repeat units or a polytetramethylene oxide structure. The block may suitably be less than about 50% by weight of the LC block copolymer, more suitably about 30% by weight or less of the LC block copolymer and most suitably about 10% by weight or less of the LC block copolymer.

The tensile strength of a typical poly(ether-block-amide) thermoplastic elastomer of the type described above has tensile strength of about 10,000 psi and DSC melting point of about 174° C.

Suitably, the LC block copolymer, to act as a reinforcing material in such a polymer blend, has a tensile strength of greater than about 10,000 psi, for example, greater than about 12,000 psi, more suitably greater than about 20,000 psi and most suitably greater than about 30,000 psi.

Thus, it is desirable to select the LC block copolymer structure so that it has a strong interaction with the thermoplastic elastomer to achieve mechanical strength enhancement through effective load/force transferring.

It is also desirable that the LC block copolymer have a melting point within a thermoplastic processing window of less than the thermal degradation temperature of the thermoplastic elastomer. In the case where the thermoplastic elastomer is poly(ether-block-amide), for example, the melting point range is suitably less than about 240° C. Extrusion/coextrusion is an example of a suitable method to process such thermoplastic materials.

The above example is intended for illustrative purposes only, and not as a limitation on the scope of the invention. Other polymers are known to those of skill in the art and may also be employed herein.

If a blend of polymers is employed, the amount of LC block copolymer is suitably about 75% or less and more suitably about 50% or less. The amount of LC block copolymer employed may be from about 5% to about 75% and more suitably about 5% to about 50% and even more suitably about 10% to about 30%.

The at least one second polymer or blend of polymers may be employed from about 25% to about 95%, more suitably about 50% to about 95% and even more suitably about 70% to about 90%.

The present compositions may be employed in the manufacture of any medical device or component thereof which is suitably formed from polymer compositions. Examples include catheter assemblies used in diagnosing and treating diseases such as vascular diseases.

The present invention finds utility in the manufacture of expandable medical balloons, particularly those employed in the cardiovascular system wherein the balloon size is very small.

Balloon formation is known in the art. In some processes, a tube of polymer material is extruded and then expanded radially and axially. Balloon formation is described in U.S. Pat. No. 4,490,421 and in commonly assigned U.S. Pat. No. 6,024,722, both of which are incorporated by reference herein in their entirety. Of course, other processes are known and may be employed in the present invention.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A catheter assembly, at least a portion of the catheter assembly formed from a polymer composition, the polymer composition comprising:
   a liquid crystal block copolymer having an A block and a B block, the A block is a mesogenic block, the B block comprising at least one member selected from the group consisting of olefins, esters, ethers, amides, and siloxanes; and
   at least one polymer which is not a liquid crystal polymer, the at least one polymer selected so as to be compatible with the B block of the liquid crystal block copolymer.

2. The catheter assembly of claim 1 comprising an expandable balloon member, the expandable balloon member is formed from said polymer composition.

3. The catheter assembly of claim 2 wherein said at least one polymer which is not a liquid crystal polymer is a poly(ether-block-amide).

4. The catheter assembly of claim 3 wherein said B block comprises amides.

5. The catheter assembly of claim 4 wherein said A block comprises the reaction product of 4-acetoxybenzoic acid and 1,4-butanediol.

6. The catheter assembly of claim 4 wherein said A block is polymerized with terephthalic acid and nylon 6.

7. The catheter assembly of claim 6 wherein said liquid crystal block copolymer is an A-B-A block copolymer having the general formula $[(ABA\text{-}BDO\text{-}ABA\text{-}TPA)_x\ ABA\text{-}BDO\text{-}ABA]\text{-}Ny6\text{-}[ABA\text{-}BDO\text{-}ABA\text{-}(TPA\text{-}ABA\text{-}BDO\text{-}ABA)_y]$.

8. The catheter assembly of claim 4 wherein said A block comprises 1,3-propane diol or ethylene glycol.

9. The catheter assembly of claim 5 wherein said A block is polymerized with a diacid terminated nylon polymer.

10. The catheter assembly of claim 6 wherein said A block is polymerized with 2,6-naphthalene dicarboxylic acid.

11. The catheter assembly of claim 5 wherein said A block is polymerized with 6-hydroxy-2-naphthoic acid.

12. The catheter assembly of claim 1, said catheter assembly comprising at least one catheter shaft, at least a portion of said at least one catheter shaft comprises said polymer composition.

13. An expandable medical balloon, the expandable medical balloon formed from at least one poly(ether-block-amide) block copolymer, the expandable medical balloon is reinforced with a liquid crystal block copolymer having at least one mesogenic A block and at least one non-liquid crystal polymer B block.

14. The expandable medical balloon of claim 13 wherein said poly(ether-block-amide) block copolymer is compatible with said non-liquid crystal polymer B block.

15. The expandable medical balloon of claim 13 wherein said B block of said liquid crystal block copolymer comprises a diacid terminated nylon polymer.

16. The expandable medical balloon of claim 15 wherein said diacid terminated nylon polymer is nylon 6, nylon 6,10 or nylon 9,12.

17. The expandable medical balloon of claim 13 wherein said B block comprises a mono-acid terminated nylon polymer and said block copolymer is an AB diblock copolymer.

18. The expandable medical balloon of claim 17 wherein said mono-acid terminated nylon polymer is nylon 12.

19. The expandable medical balloon of claim 13 wherein said mesogenic A block is nylon and said B block comprises polytetramethylene oxide.

20. The expandable medical balloon of claim 19 wherein said nylon comprises at least one aromatic group per a repeat unit.

* * * * *